United States Patent
Smith et al.

(10) Patent No.: US 10,655,104 B2
(45) Date of Patent: May 19, 2020

(54) METHOD FOR IN VIVO, EX VIVO AND IN VITRO REPAIR AND REGENERATION OF CARTILAGE AND COLLAGEN AND BONE REMODELING

(71) Applicant: The Board of Trustees of the Leland Stanford Junior University, Palo Alto, CA (US)

(72) Inventors: R. Lane Smith, Palo Alto, CA (US); Dennis R. Carter, Stanford, CA (US); David J. Schurman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 696 days.

(21) Appl. No.: 14/553,869

(22) Filed: Nov. 25, 2014

(65) Prior Publication Data

US 2015/0079048 A1   Mar. 19, 2015

Related U.S. Application Data

(60) Continuation of application No. 11/980,967, filed on Jul. 11, 2008, now abandoned, which is a
(Continued)

(51) Int. Cl.
*C12N 5/077* (2010.01)
*A61K 35/32* (2015.01)
(Continued)

(52) U.S. Cl.
CPC ........ *C12N 5/0655* (2013.01); *A61F 2/30756* (2013.01); *A61K 35/32* (2013.01);
(Continued)

(58) Field of Classification Search
None
See application file for complete search history.

(56) References Cited

U.S. PATENT DOCUMENTS

| 4,628,027 A | 12/1986 | Gay |
| 5,759,190 A | 6/1998 | Vibe-Hansen et al. |
| 5,902,785 A | 5/1999 | Hattersley et al. |

FOREIGN PATENT DOCUMENTS

WO        09844874        10/1998

OTHER PUBLICATIONS

Lafeber et al, "Intermittent Hydrostatic Compressive Force Stimulates Exclusively the Proteoglycan Synthesis of Osteoarthritic Human Cartilage" 1992, vol. 31, pp. 437-442.*
(Continued)

*Primary Examiner* — Allison M Fox
(74) *Attorney, Agent, or Firm* — Brian E. Davy; Bozicevic, Field & Francis LLP

(57) ABSTRACT

A method for in vivo, ex vivo and in vitro regeneration of cartilage and collagen. In vivo, ex vivo and in vitro regeneration and de novo formation of articular cartilage and collagen by intermittently applied hydrostatic pressure. The application of external interval loading consisting of repeated periods of applied hydrostatic pressure followed and interrupted by periods of recovery. The application of the intermittent hydrostatic pressure at physiological levels 5-10 MPA for an interval of 4 hours followed by a recovery period up to about 20 hours, said pressure applied to the cartilage cells in vitro, explants of cartilage ex vivo and in vivo to cartilage that remains intact within to joint space of diarthrotic joints. The interval loading results in the selective inhibition of matrix degrading enzymes, pro-inflammatory cytokines and chemokines that attract inflammatory cells into the joint cavity and in selective decrease of gene
(Continued)

expression of growth factors that are inhibitory to type II collagen expression.

10 Claims, 9 Drawing Sheets

Related U.S. Application Data continuation of application No. 10/328,387, filed on Dec. 24, 2002, now abandoned, which is a division of application No. 09/677,109, filed on Sep. 29, 2002, now Pat. No. 6,528,052.

(60) Provisional application No. 60/157,337, filed on Oct. 1, 1999.

(51) Int. Cl.
    *A61F 2/30*     (2006.01)
    *A61K 35/12*     (2015.01)
    *A61F 2/28*     (2006.01)
    *A61F 2/08*     (2006.01)

(52) U.S. Cl.
    CPC . *A61F 2/08* (2013.01); *A61F 2/28* (2013.01); *A61F 2/3094* (2013.01); *A61F 2240/001* (2013.01); *A61F 2310/00365* (2013.01); *A61K 35/12* (2013.01); *C12N 2500/02* (2013.01); *C12N 2521/00* (2013.01)

(56) References Cited

OTHER PUBLICATIONS

Hall, A.G., et al., "The Effects of Hydrostatic Pressure on Matrix Synthesis in Articular Cartilage," Journal of Orthopedic Research, pp. 1-10 (1991).

Handa, Tadashi, et al., "Effects of Hydrostatic Pressure on Matrix Synthesis and Matrix Metalloproteinase Production in the Human Lumbar Intervertebral Disc," SPINE, 22(10):1085-1091, (1997).

Klein-Nulend, Jenneke, et al., "Influence of Intermittent Compressive Force on Proteoglycan Content in Calcifying Growth Plate Cartilage In Vitro," The Journal of Biological Chemistry, 262(32):15490-15495, (Nov. 1987).

Kolettas, Evangelos, et al., "Expression of cartilage-specific molecules is retained on long-term culture of human articular chondrocytes," Journal of Cell Science, vol. 108, pp. 1991-1999 (1995).

Lammi, Mikko J., et al., "Expression of Reduced Amounts of Structurally Altered Aggrecan in Articular Cartilage Chondrocytes Exposed to High Hydrostatic Pressure," Biochem. J., pp. 723-730 (1994).

Lippiello, L., et al., "In Vitro Metabolic Response of Articular Cartilage Segments to Low Levels of Hydrostatic Pressure," Commerce Tissue Research, 13:99-107, (1985).

Roelofsen, Jan, et al., "Mechanical Stimulation by Intermittent Hydrostatic Compression Promotes Bone-Specific Gene Expression In Vitro," J. Biomechanics, 28(12):1493-1503, (1995).

Smith, R. Lane, "In Vitro Stimulation of Articular Chondrocyte mRNA and Extracellular Matrix Synthesis by Hydrostatic Pressure," Journal of Orthopedic Research, 14(1):53-60, (1996).

Smith, R. Lane, et al., "Time-dependent Effects of Intermittent Hydrostatic Pressure on Articular Chondrocyte Type II Collagen and Aggrecan mRNA Expression," Journal of Rehabilitation and Development, 37(2):153-161, (Mar./Apr. 2000).

Steinmeyer, Jürgen, et al., "The Proteoglycan Metabolism of Mature Bovine Articular Cartilage Explants Superimposed to Continuously Applied Cyclic Methanical Loading," Biochemical and Biophysical Research Communications, Article No. RC977641, pp. 216-221, (1997).

Suh, Jun-Kyo, "Dynamic Behavior of a Biphasic Cartilage Model Under Cyclic Compressive Loading," J. Biomechanics, 28(4):357-364 (1995).

\* cited by examiner

* 10 MPa AT 1 Hz FOR 4 HOURS ON AND 20 HOURS OFF FOR 4 DAYS.

METHOD FOR IN VIVO, EX VIVO AND IN VITRO REPAIR AND REGENERATION OF CARTILAGE AND COLLAGEN AND BONE REMODELING

CROSS-REFERENCE TO RELATED APPLICATIONS

This application is a continuation of U.S. patent application Ser. No. 11/980,967, filed on Jul. 11, 2008, which is a continuation of U.S. patent application Ser. No. 10/328,387, filed on Dec. 24, 2002, which is a divisional of U.S. patent application Ser. No. 09/677,109, filed on Sep. 29, 2000, now U.S. Pat. No. 6,528,052, which is based on and claims priority of the Provisional Application Ser. No. 60/157,337 filed on Oct. 1, 1999, all of which are hereby incorporated by reference in their entireties.

STATEMENT OF GOVERNMENTAL SUPPORT

This invention was made with U.S. Government support under Veteran's Administration Rehabilitation Research and Development Merit Review Grant No. A857-RC. The U.S. Government has certain rights in this invention.

BACKGROUND OF THE INVENTION

Field of the Invention

This invention concerns a method for in vivo, ex vivo and in vitro repair, regeneration, de novo formation and remodeling of diseased and normal mesenchymal or mesenchymally derived cells, cartilage, collagen and bone. In particular, this invention concerns in vivo, ex vivo and in vitro regeneration of articular cartilage and collagen and bone remodeling by intermittently applied hydrostatic pressure. The method involves the application of external interval loading consisting of repeated periods of applied hydrostatic pressure followed and interrupted by periods of recovery. The method specifically concerns application of the intermittent hydrostatic pressure at levels 0.5-30 MPa for an interval of 1-8 hours followed by a recovery period up to about 16-23 hours, said pressure applied to cartilage and bone cells in vitro, explants of cartilage and bone graft ex vivo and in vivo to cartilage that remains intact within the joint space of diarthrotic joints, or in vivo to the bone. The interval loading results in significant increase in expression of proteins providing the unique phenotypic properties of cartilage and bone and in the selective inhibition of matrix degrading enzymes, pro-inflammatory cytokines and chemokines that attract inflammatory cells into the joint cavity and in selective decrease of gene expression of growth factors that are inhibitory to extracellular matrix repair and regeneration.

The invention also concerns methods for treatment of articular cartilage and collagen regeneration, restoration and transplantation.

Background and Related Disclosures

Arthritic diseases, particularly osteoarthritis, affect more people than any other ailment. Osteoarthritis involves loss of function of cartilage which undergoes a slow progressive degeneration in many joints. Although osteoarthritis is considered a non-inflammatory disease a certain degree of inflammation occurs. Osteoarthritis is distinguished from the rheumatoid arthritis which is a chronic inflammatory joint disease.

Osteoarthritis affects most people in late middle age. Osteoarthritic related conditions decrease personal productivity and quality of life and in an aging society, increase the morbidity and mortality for men and women by increasing the incidence of other chronic conditions, such as, for example, osteoporosis. Currently, the only successful treatment for end stage joint disease requires major surgery involving total joint replacement which is not without associated complications such as infection, aseptic loosening, and pain. These complications can then lead to the necessity for revision arthroplasty. Reversal of early onset osteoarthritis by novel surgical techniques that would abrogate the necessity for joint replacement is just now being tried in experimental stages.

Intra-articular surgical approaches are being developed that entail transfer of cartilage cells from healthy regions of the joint to diseased surfaces in order to restore joint function. In this context, cartilage cells or small regions of cartilage are placed in partial or full-thickness defects within the joint surface using an open surgical procedure. The cell construct is then held in place by periosteal tissue that is sutured in place. However, implanting cells or resurfacing with autogenous or allograft cartilage in the absence of an organized extracellular matrix does not support normal weight bearing. In many cases, these grafts quickly become fibrillated and degrade. In an alternative procedure, mosaicplasty involves moving multiple small grafts of cartilage from one area of the joint surface to another to facilitate a return to weight bearing. With any type of cartilage exchange, efficacy of repair will be greatly facilitated following restoration of an extra-cellular matrix structure of normal cartilage prior to use.

Cartilage, collagen and bone diseases, therefore, present a major medical problem, particularly with an increasing aging population which is more prone to osteoarthritis and other joint regenerative diseases, and it would thus be important to have available a means for regeneration of articulate cartilage and collagen and bone remodeling.

Articular cartilage covers the ends of long bones and is load-bearing tissue that distributes forces across joint surfaces protects the more rigid underlying bone and provides smooth articulation and bending of the joints during normal activities of daily living.

Attempts are continuously made to regenerate articular cartilage. U.S. Pat. No. 6,080,194, for example describes a collagen template formed by combining a porous collagen sponge with a collagen membrane. U.S. Pat. No. 5,786,217 describes methods and compositions for the repair of articular cartilage defects. U.S. Pat. No. 5,206,023 discloses methods and compositions for treatment and repair of defects or lesions of the cartilage. U.S. Pat. No. 5,041,138 concerns neomorphogenesis of cartilage in vivo from cell culture for the growth and implantation of cartilaginous structures. However, none of these patents disclose a method which would regenerate the diseased cartilage to a functional state and such method is still lacking.

Clinical experience in humans and experimental studies with animal models confirm that mechanical loads provide an essential stimulus for maintenance of normal articular cartilage homeostasis (*Proc. Soc. Exp. Biol. Med.*, 190:275 (1989)).

Alterations in joint loading due to immobilization (*Clin. Orthop. Rel. Res.*, 219:28 (1987)) ligamentous laxity (Ibid, 213:69 (1986)), excessive impact (*J. Biomechanics*, 6:51

(1973)) or increased subchondral bone stiffness (*J. Biomechanics*, 28:357 (1995)) result in pathological changes in cartilage characteristic of osteoarthritis.

The ability of cartilage to change shape rapidly and reversibly is attributable to a resilient and elastic matrix with a high content of highly soluble proteoglycans which are entrapped in collagen, an insoluble fiber network. Proteoglycans, collagen and other molecules present in the cartilage tissue are produced by mesenchymally-derived cartilage cells, the chondrocytes.

In vitro studies confirm that the cartilage cells, the articular chondrocytes, respond to specific loading conditions through an anabolic or catabolic reaction that is attributable to the stress and strain imparted to the cell by the physical stimulus (*Biochem. Biophys. Res. Commun.*, 240:216 (1997); *Spine*, 22:1085 (1997) and *J. Orthop. Res.*, 15:189 (1997)).

Recognition of the role that mechanical loading plays in the regulation of articular chondrocyte metabolism has been delineated in part by mathematical analysis of the distribution of forces across joint surfaces (*J. Biomech.*, 22:853 (1989)).

Biomechanical analyses described in *J. Exp. Physiol.*, 81:535 (1996) confirm that chondrocytes in the cartilage of a diarthrotic joint experience levels of hydrostatic pressure in the order of 7 to 10 MPa that result from normal activities of daily living. Studies examining the influence of mechanical forces on tissue differentiation revealed that increased cartilage thickness occurs in regions of the diarthrotic joint exposed to high intermittent compressive hydrostatic stress. Thinner cartilage coincides with regions experiencing decreased hydrostatic pressure and having tensile forces arising tangential to the joint surface (*Bone*, 11:127 (1990)).

Experimental studies described in *J. Orthop. Res.*, 9:1-10 (1991) confirmed that hydrostatic pressure influences articular cartilage matrix metabolism when applied in vitro and established that hydrostatic pressure at levels of 5-15 MPa modulates $^{35}SO_4$ and $^3H$-proline incorporation rates into adult bovine articular cartilage in vitro.

Organ culture experiments described in *J. Biol. Chem.*, 262:15490 (1987) demonstrated that sites of proteoglycan production coincide with regions of pure hydrostatic pressure. Physiological levels of hydrostatic pressure enhance mRNA signal levels for aggrecan and type II collagen when measured immediately after loading as described in *J. Orthop. Res.*, 14:53 (1996). In a study of load controlled compression of aggrecan mRNA expression in bovine cartilage explants a transient up-regulation was observed after 1 hour of loading.

While the above research describes and recognizes the importance of the hydrostatic pressure on normal function of cartilage and type II collagen, such knowledge was nevertheless impossible to apply clinically because the continuous application of the hydrostatic pressure leads to exhaustion of the cartilage metabolic potential and its damage while the brief (<1 hour) of loading with hydrostatic pressure leads to varied cellular response which disturbs the chondrocyte metabolism and homeostasis. For example, a short period of hydrostatic pressure loading results in increased expression of type II collagen mRNA while the continuously applied load does not maintain such increased expression. On the other hand, the aggrecan signal expression continued to increase throughout the duration of the load. Clearly, these results disturb the cellular equilibrium between aggrecan and type II collagen. Cartilage cells respond to multiple stimuli in unpredictable ways and variability of the response depends on time, magnitude and frequency of loading.

Clearly, this unpredictability prevents using the continuous long or short periods of indiscriminate hydrostatic pressure loading for treatment of osteoarthritis or regeneration of damaged cartilage (*J. Rehab. Res. Dev.*, 37:153-161 (2000)).

In view of the severity and disabling effect of osteoarthritis and other cartilage, collagen or bone diseases, it would be important to provide a method which would permit a cartilage or collagen regeneration and bone remodeling.

Until recently, it was believed that articular cartilage can no longer repair itself once the arrangement of the supporting fibers has been disrupted. (*Articular Cartilage and Osteoarthritis*, Workshop Conference Hoechst and Werk, Kalle-Albert, Wiesbaden May 12-16, 1991, Eds. Kuettner et al., Rosen Press, New York.

It has now been found that such regeneration is possible with a specific regimen of intermittently applied hydrostatic pressure to mesenchymal or mesenchymally-derived cells, such as fibroblasts, fibrochondrocytes or chondrocytes and it is, therefore, a primary objective of the current invention to provide a method for treatment of osteoarthritis and other cartilage and collagen diseases by stimulating their regeneration, de novo formation, and bone remodeling, said method providing a defined mechanical loading environment which regenerates and repairs adult cartilage and bone cells.

All patents, patent applications and publications cited herein are hereby incorporated by reference.

BRIEF SUMMARY OF THE INVENTION

One aspect of the current invention is a method for repair, regeneration and de novo formation of cartilage, replenishment of chondrocytes, or deposition of type II collagen and stimulation and bone remodeling.

Another aspect of the current invention is a method for treatment of diseases of cartilage, collagen or bone by stimulating the cartilage and collagen regeneration and bone remodeling using an interval loading regimen consisting of repeated periods of intermittently applied hydrostatic pressure within specified loading interval followed by a recovery period.

Still another aspect of the current invention is an in vivo, ex vivo or in vitro method for repair, regeneration and de novo formation of cartilage wherein the regeneration is achieved by applying an interval loading regimen consisting of repeated periods of applied hydrostatic pressure followed by periods of recovery to in situ or ex situ cartilage or cartilage cells or to cartilage or cartilage cells in vitro.

Still yet another aspect of the current invention is an in vivo or ex vivo cartilage repair, regeneration and de novo formation method which involves applying hydrostatic pressure to the cartilage tissue in need of regeneration in situ or to cartilage removed from in situ or chondrocytes, fibroblast or fibrochondrocytes adhered to a matrix and subjected to the regimen comprising applying intermittently the hydrostatic pressure for about 1-8 hours followed by about 16-23 hours of recovery period.

Still yet another aspect of the current invention is an in vivo collagen restoration method which involves applying hydrostatic pressure to the cartilage, cartilage cells, other mesenchymally-derived cells or collagen tissue in need of repair and regeneration.

Still yet another aspect of the current invention is an in vivo bone restoration method which involves applying hydrostatic pressure to the bone site in need of regeneration of cartilage as a progenitor tissue or direct mechanical stimulus using a regimen comprising applying, intermittently, the hydrostatic pressure to the bone osteoblast cells for about 1-8 hours, followed by recovery period of about 16-23 hours.

Still yet another aspect of the current invention is a diseased joint regeneration method wherein cartilage grafts that are submitted to the intermittent hydrostatic pressure loading and restored to a healthy load-bearing matrix are placed in a diseased joint to restore its normal function.

Still yet another aspect of the current invention is a regenerated functional healthy load bearing cartilage from the diseased cartilage wherein said diseased cartilage is subjected to intermittent hydrostatic pressure followed by periods of recovery until the normal mechanical and biochemical properties are restored.

Still yet another aspect of the current invention is a method for detection of functionality of the cartilage by determining relative levels of, or levels of expression of, cartilage or bone degradative enzymes, cytokines and their inhibitors or growth promoting substances, growth factors and hormones, following subjecting the diseased cartilage or bone to intermittent hydrostatic pressure followed by periods of recovery.

DEFINITIONS

Figure 1:
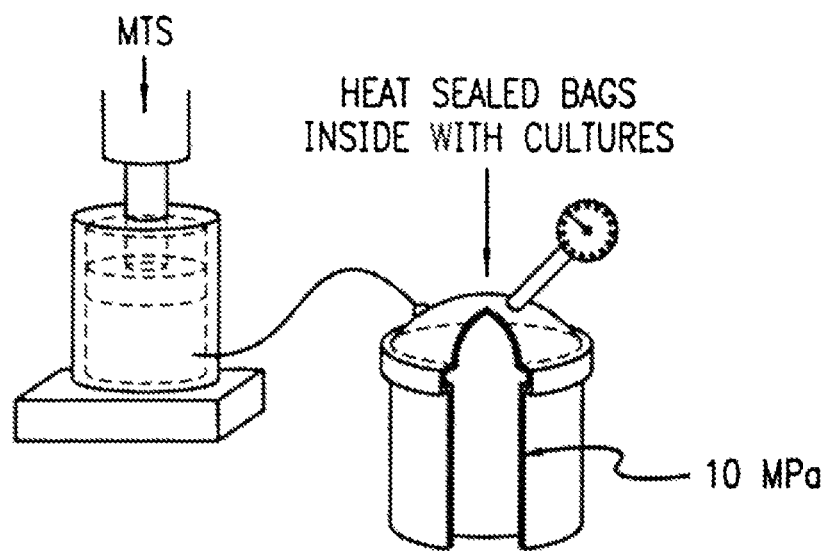
FIG. 1 is a schematic of a servo-hydraulic loading instrument suitable for application of intermittent hydrostatic pressure to articulate chondrocytes.

As used herein:

"Cancellous" means bone that has a lattice-like or spongy structure.

"Mesenchymal", "mesenchymal stem cells" or "mesenchymally-derived cell" means the cells that are located within and produce the extracellular matrix of cartilage (chondrocytes), connective tissue (fibroblasts), fibrocartilage (fibrochondrocytes), tendon (tenocytes) and bone (osteoblasts and osteocytes).

"Loading interval" means a period of applied IHP load, or stimulus in tissue, that is followed by a recovery period where no external pressure is applied and where the pressure returns to the ambient condition.

"Interval" means a combination of a load and recovery periods repeated as many times as needed.

"De novo formation" means production of cartilage connective tissue, fibrocartilage, tendon and bone as a result of adherence by chondrocytes, fibroblasts, fibrochondrocytes, tenocytes and osteoblasts within a support structure (scaffold or collagen matrix) following exposure to loading interval.

"Osteoblast" means a bone forming cell derived from mesenchyme (fibroblast) and forms an osseous matrix in which it becomes enclosed as an osteocyte.

"Fibroblast" or "fibrocyte" means a stellate or spindle-shaped cell with cytoplasmic processes present in connective tissue capable of forming collagen fibers.

"Aggrecan" means a large aggregating proteoglycan that plays a role in imparting compressive resilience to the articular cartilage and enable load bearing. Aggrecan is the abundant proteoglycan which represents about 85% of all total proteoglycans.

"Type II collagen" means a homopolymeric molecule of α1 (11) chains which is the product of a single gene COL2A1. Type II collagen is the most abundant of all other collagen types and represents about 95% of the total collagen.

"Matrix metalloproteinase" or "MMP" means a protease which causes and is associated with cartilage degeneration in a diseased joint. MMP may be further distinguished as MMP-1, MMP-2, MMP-9, etc.

"Macrophage chemoattractant protein-1" or "MCP-1" means a pro-inflammatory mediator that influences the immune state of tissue. Its increased level is associated with the beginning or increase of tissue destruction, its decreased level is associated with decrease of tissue damage or healing.

"Transforming Growth Factor-β" or "TGF-β" means a factor released by the cells upon applying intermittent hydrostatic pressure and signifies a change in the cell metabolism.

"Fibroblast growth factor 1" or "FGF-1" means a growth factor which is not known to be involved in chondrocytes or osteoblast-like cells proliferation.

"MPa" means MegaPascal. One MPa is equal to 145 psi.

"GAG" means glycosaminoglycans.

"HIP" means intermittent hydrostatic pressure.

"GAPDH" means glyceraldehyde-3-phosphate dehydrogenate.

"APMA" means 4-aminophenylmercuric acetate, an activator of latent proenzyme to the active enzyme.

DETAILED DESCRIPTION OF THE PREFERRED EMBODIMENT

The invention described herein concerns a discovery that intermittently and repeatedly applied hydrostatic pressure during interval loading periods influences articular chondrocyte gene expression, elicits load-dependent collagen type II expression, decreases a matrix metalloproteinase expression, results in regeneration of diseased or damaged cartilage and collagen, permits the de novo formation of mesenchymal or mesenchymally-derived cells within a matrix and alters bone remodeling. The discovery is suitable for repair and treatment of degenerative joint diseases such as osteoarthritis, arthrosis, injuries to the joint cartilage, degenerative joint disease, joint replacement, bone restructuring and other diseases of cartilage, collagen and bone.

I. Method for Cartilage and Collagen Regeneration and Bone Remodeling

The method for cartilage and collagen regeneration and bone remodeling for treatment of the above listed diseases comprises, in its broader scope, the application of interval loading regimen according to the invention to a site of injury in vivo, to a transplantable full-thickness grafts of human osteoarthritic or diseased cartilage or bone ex vivo or to the cells isolated from the healthy or diseased cartilage, collagen and bone in vitro.

A. Therapeutic Regimen for Cartilage Regeneration

General Conditions

The therapeutic regimen consists of stimulation of treated tissue or isolated cells with repeated periods of applied hydrostatic pressure followed by periods of recovery (loading interval). Pressure is preferably applied intermittently within each loading interval. Method parameters, such as, pressure, a frequency, length of intervals, intermittence and recovery period, are selected based on the chosen method for regeneration, that is, in vivo, in situ, ex vivo, or in vitro, as well as on the disease and on the seriousness of the cartilage degeneration.

1. Hydrostatic Pressure

The loading regimen suitable for repair, regeneration or de novo formation of intact cartilage, intact bone, cartilage and bone graft or cells generally comprises the application of hydrostatic pressure between 0.5 MPa and 30 MPa, preferably between 1 MPa and 20 MPa, and most preferably between 5 MPa and 10 MPa in intermittent intervals of 1 Hz frequency.

Typically, pressures higher than about 30 MPa are not used or recommended as they can lead to cell damage, while pressures lower than 0.1 MPa may not be effective for the regeneration of cells or tissue. Pressures around 5-10 MPa correspond to normal physiological levels encountered by articular cartilage in vivo.

2. Duration of IHP and Recovery Periods

The duration of the high pressure intervals generally range from minutes to about 8 hours, and are preferably between about 1 and 8 hours, most preferably about 4 hours.

During the recovery period, the tissue/cells of interest are exposed to atmospheric or sufficiently low constant pressure. The recovery periods can generally range from minutes to tens of hours, and are preferably between about 16 to about 23 hours, preferably about 20 hours.

3. Frequency

Within each intermittent hydrostatic pressure interval, the pressure is applied intermittently with a frequency between 0.1 Hz, and 10 Hz, preferably on the order of 1 Hz. In the preferred embodiment for cartilage cells, the interval loading regimen is applied for at least 4 consecutive days, typically for about 4 hours of loading at 10 MPa applied at 1 Hz followed by about 20 hours of recovery at constant atmospheric pressure.

4. Length of Treatment

The length of the treatment of cartilage depends entirely on the degree and seriousness of cartilage degeneration, extent of collagen loss, severity of bone disease, or degree and seriousness of joint injury. Typically, the improvement in cartilage functionality and its regeneration is observed after about four treatments with IHP loading, that is, typically after 4 days of treatment. In more degenerate, diseased or injured cartilage, such treatment is continued for as long as 100 days without any negative consequences and may be continued indefinitely when cartilage and/or collagen function is chronically impaired. Preferable treatment will last and be successful in between 7 and 30 days.

For de novo formation, the collagen matrix is laden with healthy or diseased cells to be treated and the treatment is continued until the new tissue is formed.

5. Functionality Testing

The length of treatment depends on the rapidity of functional recovery. Functionality of cartilage depends on the recovery and/or rebuilding and/or formation of load-bearing matrix. Degeneration of cartilage results from deformation of cells, from inappropriate levels of shear stress loading to matrix, and degeneration due to metabolic shifts.

These metabolic shifts affect genetic expression of cartilage cell with respect to aggrecan and collagen, particularly type II collagen, and certain growth factor such as TGF-β. The shifts and chondrocyte metabolism also lead to expression or over expression of proteins which are not normally expressed or are less expressed in healthy functional chondrocytes, such as metalloproteinases MMP-1, MMP-2, MMP-9 and pro-inflammatory cytokines, such as IL-1 and IL-6.

Consequently, during and particularly after the IHP loading treatment, some or all of the above factors are tested and their presence is evaluated for increased activity. Absence or decreased activities are correlated with the regeneration of cartilage integrity and load-bearing function.

TABLE 1

| | | | Functionality Testing | | | | | |
|---|---|---|---|---|---|---|---|---|
| | Aggrecan | Type II Collagen | MMP-2 | MMP-1 | MMP-9 | IL-6 | IL-1 | MCP-1 |
| Physiological Levels | 4-7% Wet wt | 10-29% wet wt. | Low | low | nd | low | nd | low |
| Pathological | 0.1-1% | 1-10% | High | high | elevated | high | elevated | high |

TABLE 1-continued

Functionality Testing

| | Aggrecan | Type II Collagen | MMP-2 | MMP-1 | MMP-9 | IL-6 | IL-1 | MCP-1 |
|---|---|---|---|---|---|---|---|---|
| Levels | wet wt. | wet wt. | | | or high | | | |
| Regenerated Levels | 4-7% | 10-20% | Low | low | nd | low | nd | low | nd = not detectable or trace

Functionality testing disclosed herein involves determination of relative values of extracellular matrix components such as aggrecan and type II collagen, proteases such as MMP-1, MMP-2, MMP-9 and cytokines such as IL-6, IL-1 and MCP1. These values differ depending on the tissue preparation and the method used but the trend remains the same, namely, levels of extracellular matrix proteins decrease and levels of proteases and cytokines increase in injured or degenerated cartilage and collagen. During regeneration, the levels are returning to their normal physiological ranges.

The loading regimen applied according to the invention was found to stimulate the regeneration of articular cartilage tissue, collagen tissue, bone tissue and/or their respective isolated cells. The interval loading regimen was also found to increase gene expression for proteins that form the functional extracellular matrix of articular cartilage. After application of an interval loading regimen of the present invention, staining of the matrix with cationic dyes confirmed the increased presence of extracellular matrix.

Additionally, the interval loading regimen was found to result in the selective inhibition of matrix-degrading enzymes, pro-inflammatory cytokines and chemokines that attract inflammatory cells into the joint cavity. Furthermore, the interval loading regimen was found to selectively decrease gene expression for growth factors inhibitory to type II collagen expression and was also found to affect expression of transforming growth factor-β1 (TGF-β1), a matrix metalloproteinases such as, for example, MMP-1, MMP-2, MMP-9 and tissue inhibitor of metalloproteinase (TIMP) in human osteoblast-like cells. These and other factors may be conveniently used for assessment of cartilage and bone functionality as shown in Table 1.

The methods which are used for detection of the parameters for determination of functionality include but are not limited to RT-PCR, zymography, biochemistry, staining, ELISA, gene array techniques and proteomics.

B. In Vitro Treatment

For in vitro treatment, damaged cartilage tissue is removed from a patient by surgical means. The interval loading regimen can be applied to the intact tissue such as osteochondro cartilage graft for ex vivo treatment. For in vitro treatment, the normal or diseased cartilage matrix is degraded and the interval loading regimen is applied to the resulting cartilage cells cultured in suspension within scaffold/support or as monolayers. After the application of the loading regimen, the resulting de novo formed tissue or collection of cells is re-implanted into a patient. Preferably, but not necessarily, the transplant is autologous.

The surgical procedure generally follows the technique that has been developed and used for arthroscopic intervention using osteochondral grafting. In this procedure, a full-thickness sample of cartilage is removed from peripheral regions of the joint surface and is then transferred into a circular defect. The host site typically has a circumference that is smaller than the material to be inserted so that the union between the host site and the replacement tissue is a resistance fit. In the material to be produced in response to interval loading, the restored cartilage material is adjusted in size to match the surface contours of the joint. This is different from the usual procedure of osteochondral grafting where the oversized graft is left 2-3 mm above the surface of the surrounding cartilage. The formation of a type II collagen-based extracellular matrix that is capable of resisting normal joint loads permits press-fit grafts to match the normal joint surface thickness that coincide with the natural thickness that corresponds to the regional variation of the normal joint.

In vitro treatment of cells, cell monolayers or cell cultures is essentially as described in section II.

C. Ex Vivo Treatment

For ex vivo treatment, which is particularly suitable for treatment of joint cartilage injury, such as shredded or torn meniscus where only a part of the cartilage may be damaged and the rest of the cartilage is healthy and functioning, the torn or shredded cartilage is surgically removed as a cartilage graft and subjected to IHP loading regimen. Functionality of the cartilage graft is periodically tested until the criteria reach normal healthy cartilage levels as shown in Table 1. Then, the graft which retains its original shape and size is re-implanted into the joint. The IHP ex vivo treatment, testing, surgical removal and re-implantation is performed under sterile conditions.

The advantage of the ex vivo treatment is that the tissue is autologous, only the damaged tissue is subjected to treatment and the explant shape and size remains the same so that there is no less or more cartilage tissue added. Additionally, the tissue is retransplanted only if and when it is fully regenerated. The disadvantage of this approach is a double surgery. However, in extensive articular joint injury, this approach is still preferable to joint replacement or leaving the joint without cartilage or a part of the cartilage altogether.

D. In Vivo Treatment

Suitable in vivo cartilage restoration or bone remodeling methods include applying described hydrostatic pressures to the cartilage tissue or bone of the patient's joints and/or limbs, according to an interval loading regimen of the present invention. The manipulation may be done manually by a physical therapist, or automatically by a powered device.

E. Apparatus for Intermittent Hydrostatic Pressure Loading

Instruments and apparatuses for the regeneration of articular cartilage matrix and/or cells, in in vivo, ex vivo and in vitro treatments essentially comprise of a hydrostatic pressure generator, a frequency counter, a timer and a temperature control device.

A suitable in vitro apparatus comprises a pressurization chamber for holding the tissue, cells of interest or cell cultures, a hydraulic loading instrument (pressurization device) in fluid communication with the pressurization chamber, for pressurizing the pressurization chamber to predetermined pressures of interest, and control electronics for frequency control in electrical communication with the loading instrument for controlling the loading instrument to apply a predetermined interval loading regimen to the tissue or cells of interest.

A suitable instrument for application of intermittent hydrostatic pressure to isolated articular chondrocytes for treatment in vitro is seen in FIG. 1. The particular instrument seen in FIG. 1 is a commercially available stainless steel pressure vessel interfaced to a servo-hydraulic loading instrument. This design provides for the complete evacuation of air from the system resulting in application of purely hydrostatic pressure.

The apparatus seen in FIG. 1 is exemplary only and it should be understood that any instrument and apparatus, regardless of how modified, comprising similar components and providing similar results, is intended to be within the scope of this invention. A suitable in vivo instrument comprises a holder for holding a patient's joint or limb or attaching means to the patient's tissue, a motor coupled with the holder for moving the holder along a predetermined path, and control electronics electrically connected to the motor, for controlling the motor to move the patient's limb so as to apply an interval loading regimen of the present invention to the cartilage tissue of interest.

The in vivo loading of the joint is carried out by a device that spans the diarthrodial joint in question. For example, for the knee, the apparatus spans the distance from the hip to the bottom of the foot, with corresponding restraints to maintain the leg in extension. The device includes a contracting mechanism by which the femoral condylar cartilage can be juxtaposed on the tibial plateau cartilage across the meniscus at frequency between 0.1 and 10 Hz and will generate pressures in the range of 1 to 20 MPa for prescribed intervals between 1 and 8 hours, more closely approximating 4 hours per day at normal daily activity.

II. Interval Loading of Human Normal and Osteoarthritic Chondrocytes

The major component of mechanical loads to which an articular chondrocytes are exposed within the extracellular matrix of joint cartilage is hydrostatic pressure. The normal loading of joints during daily activities causes the articular cartilage to be exposed to high levels of intermittent hydrostatic pressure. Studies described in this section show that osteoarthritic chondrocytes maintained in vitro respond to applied hydrostatic pressure by increasing a positive metabolic activity and decreasing of expression of destructive enzymes.

Effect of intermittent hydrostatic pressure on cartilage matrix protein synthesis in isolated adult human articular chondrocytes focused on the mRNA expression of type II collagen, aggrecan and other degradative and growth promoting proteins, such as, MMP-2, TGF-β, MCP-1 and FGF-1. Results of these studies are seen in FIGS. 2-7.

In this series of studies, mRNA expression of aggrecan, type II collagen, MMP-2, TGF-β, MCP-1 and FGF-1 of normal healthy and osteoarthritic human chondrocytes stimulated with 1 MPa or 10 MPa hydrostatic pressure for 5 minutes or 4 hours for 4 days was compared to the mRNA expression in controls. When the loading was performed as dose response manner ranging from 1, 5 and 10 MPA vis-a-vis the hydrostatic pressure limited either to intermittent 5 minutes or intermittent 4 hours per day at 1 MPA and 10 MPA pressure, aggrecan mRNA signal was observed to increase with loads at 1 MPa, 5 MPa and 10 MPA, as seen in FIG. 2.

Figure 2A:
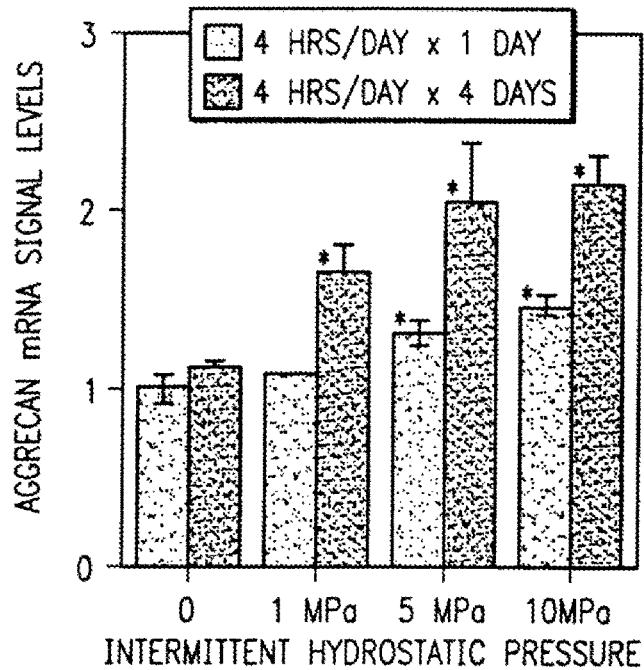
FIG. 2A-2B is a graph illustrating effects of interval loading with different magnitudes of intermittent hydrostatic pressure on aggrecan (FIG. 2A) and type II collagen (FIG. 2B) expression in normal human articular chondrocytes.
Figure 2B:
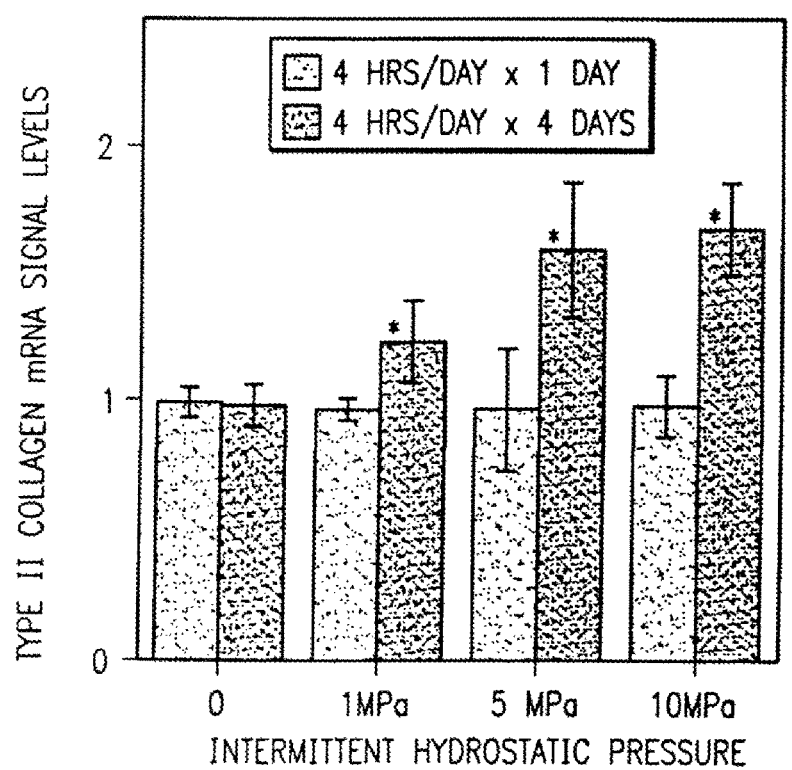

The results seen in FIG. 2A-2B clearly confirm that the current interval loading regimen results in increased genetic expression of aggrecan and type II collagen. Aggrecan is large and most abundant aggregating proteoglycan that plays a fundamental role in imparting compressive resilience to the articular cartilage and enables load bearing to persist. Type II collagen provides the tissue with tensile strength. The treatment of the invention thus leads to increased resilience of cartilage and ability to bear larger loads.

Figure 3A:
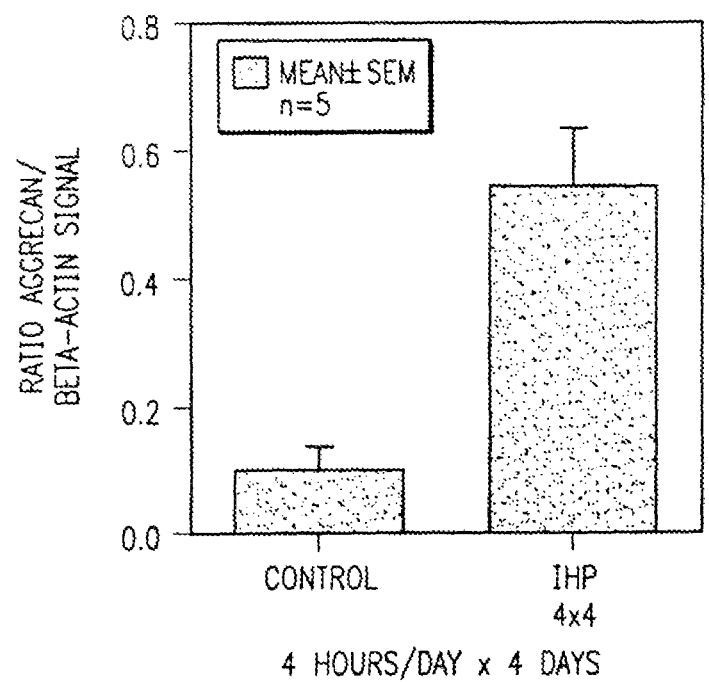
FIG. 3A-3B is a graph illustrating the effects of interval loading for 4 hours for 4 days with 10 MPa of intermittent hydrostatic pressure on the expression of aggrecan (FIG. 3A) and type II collagen (FIG. 3B) mRNA signal in human osteoarthritic articular chondrocytes.
Figure 3B:
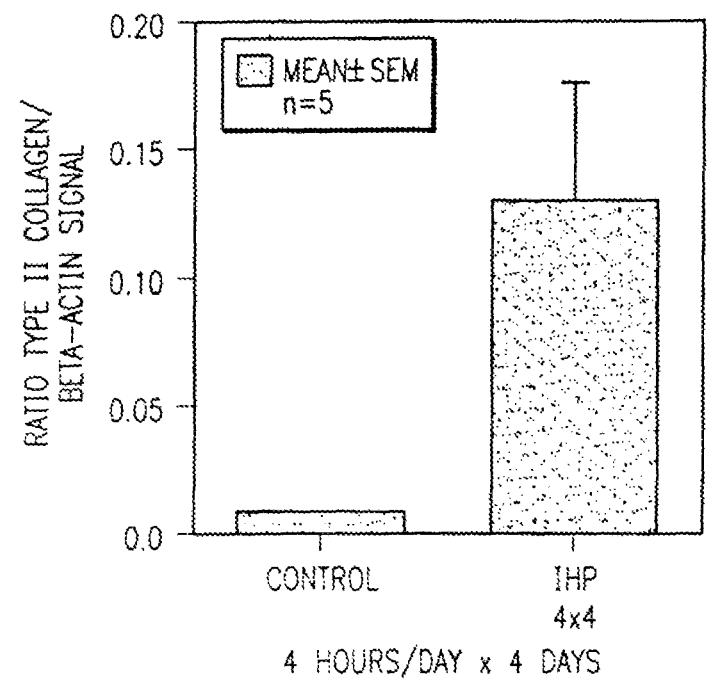

FIG. 3A-B shows the effects of 4 hour interval loading for 4 days with 10 MPA of intermittent hydrostatic pressure (IHP) on the expression of aggrecan and type II collagen mRNA signal expressed as a ratio aggrecan or type II collagen to intracellular reference protein β-actin of in human osteoarthritic articular chondrocytes.

These results clearly confirm that expression of both aggrecan and type II collagen, the major macromolecular proteins in the cartilage extracellular matrix, was increased in diseased osteoarthritic human cartilage cells following IHP treatment.

As seen in FIGS. 3A and 3B, application of intermittent hydrostatic pressure resulted in increased ratio of production of aggrecan to β-actin signal from about 0.1 to about 0.5, that is, about 5 times increase. Ratio of type II collagen to β-actin signal increased even more from about 0.01 to about 0.12 as seen in FIG. 3B.

Immunohistochemical analysis of the effect of hydrostatic pressure on chondrocytes was also investigated. Immunohistochemistry provides an index of the extracellular matrix response to mechanical loads. With loading conditions described above, immunohistochemical analysis showed that application of hydrostatic pressure increased extracellular matrix deposition of proteoglycan and collagen (data not shown).

To investigate whether IHP might also have effects on expression of molecules deletions to cartilage, a series of experiments were carried out to evaluate the release and effective interval loading of proteases and growth factors.

The effect of interval loading with intermittent hydrostatic pressure on inhibition of matrix metalloproteinase mRNA expression was determined by testing the effects of hydrostatic pressure under the same conditions as described in FIG. 2A-2B.

Figure 4A:
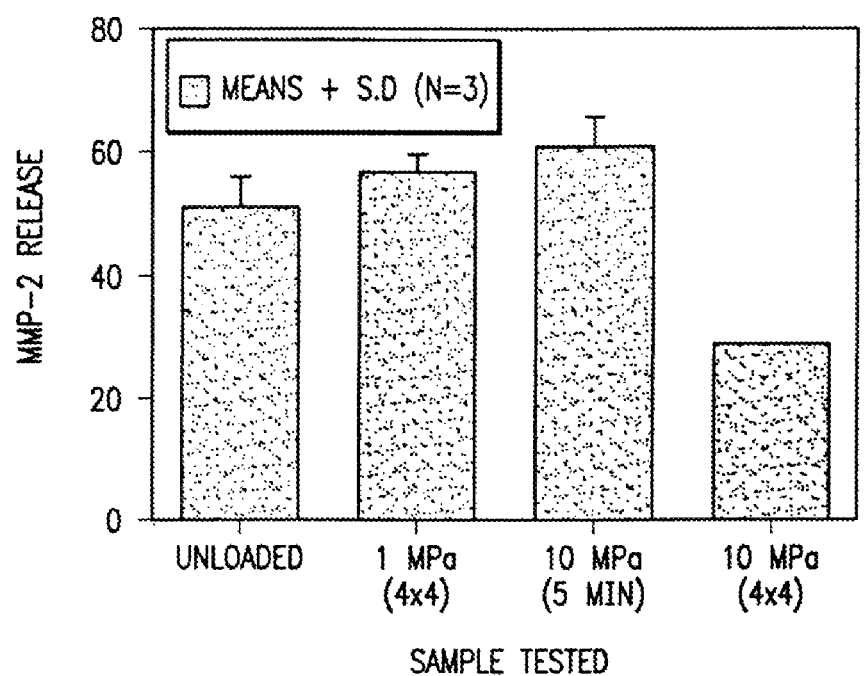
FIG. 4A-4B is set of a graphs showing the effects of interval loading with different magnitudes of intermittent hydrostatic pressure on matrix metalloproteinase-2 release from normal human articular chondrocytes using ELISA (FIG. 4A) and enzymatic activity using zymograph for activated (+APMA) and inactivated preparation (FIG. 4B).
Figure 4B:
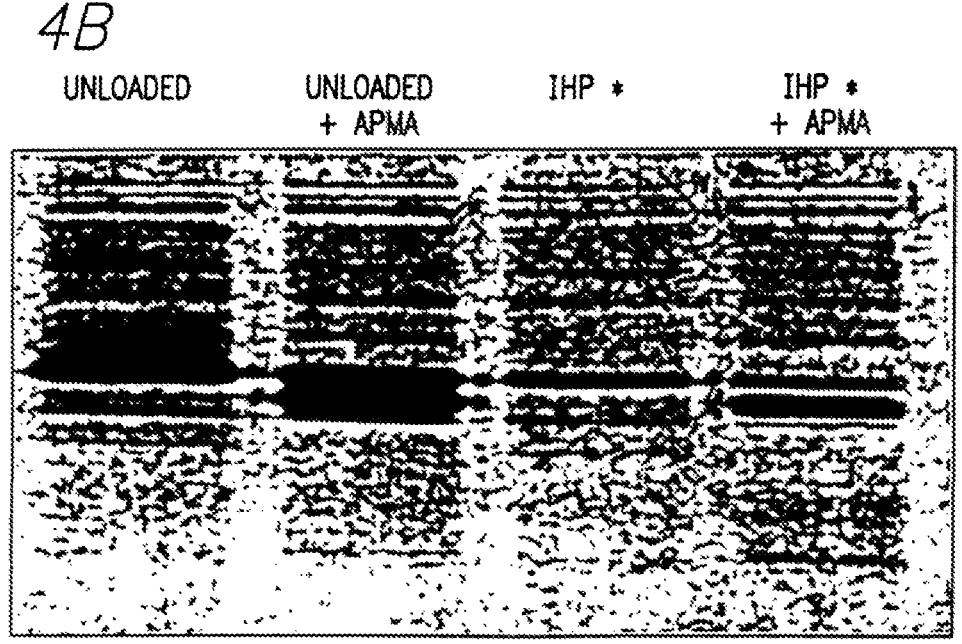

Results are seen in FIG. 4A, 4B, which shows the effects of interval loading with different magnitudes of intermittent hydrostatic pressure on matrix metalloproteinase-2 release from normal human articular chondrocytes.

Matrix metalloproteinase-2 (MMP-2) degrades the extracellular matrix collagen and is one of the several enzymes that are known to be associated with cartilage degeneration in a diseased joint. Reduction in levels of this enzyme following the application of IHP at 10 MPa for four hours for 4 days shows that repair and regeneration of the extracellular matrix is in progress. Zymographic analysis, seen in FIG. 4B, of neutral metalloproteinase expression showed that APMA subjected to intermittent hydrostatic pressure for 4 hours followed by 20 hours recovery for 4 days decreased the levels of gelatinolytic activity.

Transforming growth factor β1 (TGF-β1) is known to be involved in metabolic changes associated with the accelerated matrix resorption which occurs, for example, in osteoarthritis where both anabolic and catabolic pathways of aggrecan metabolism are activated. TGF-β1 thus affects cartilage homeostasis.

The role of TGF-β1 is most pronounced on progenitor cells, such as, for example, the surrounding periosteal region of bone. The direct effects of TGF-β1 on isolated cartilage cells vary depending on the level of produced protein since it exhibits pleiotrophic actions of different cells. The addition of TGF-β1, to articular cartilage cells in culture decreases type II collagen expressions which is counter productive to matrix production.

Figure 5:
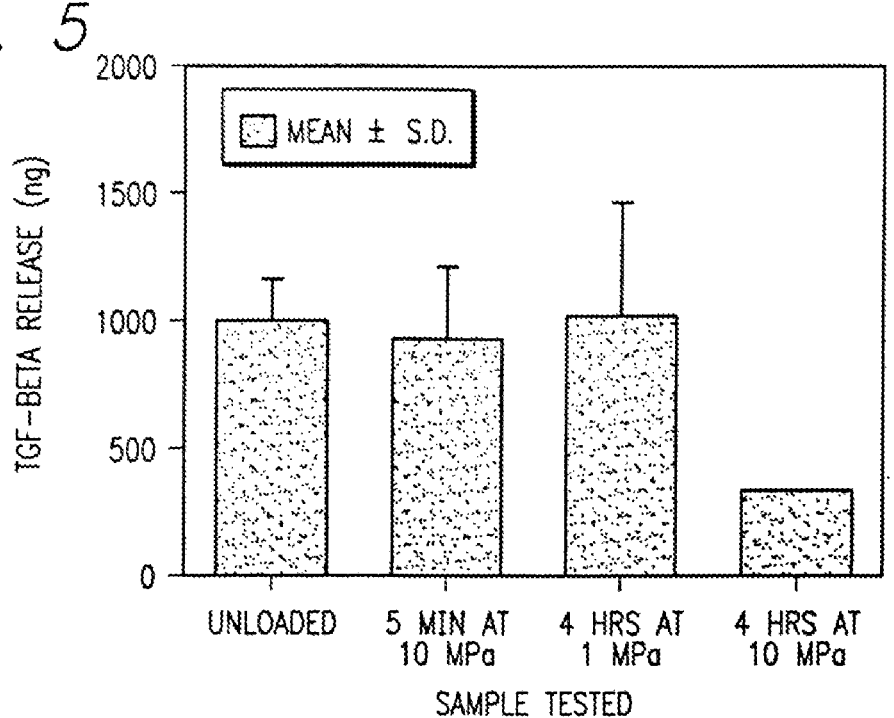
FIG. 5 is a graph showing the effects of interval loading with different magnitudes of intermittent hydrostatic pressure on release of transforming growth factor-β (TGF-β) from normal human articular chondrocytes.

FIG. 5 shows the effects of interval loading with different magnitudes of intermittent hydrostatic pressure on TGF-β1 release from normal human articular chondrocytes.

The effect of intermittent hydrostatic pressure on the release of TGF-β seen in FIG. 5 means that the cell metabolism is modulated by the mechanical stimulus. The decreased production of this growth factor is clearly coupled to other changes in the cell metabolism.

As seen in FIG. 5, the application of IHP for 4 hours at 10 MPa results in significant decrease released TGF-β from normal chondrocytes showing that protein synthesis decreases with higher pressure (10 MPa) applied intermittently for longer periods. These results establish that IHP stimulation differentially influences the metabolic state of chondrocytes in a time and dose-dependent manner. As will be seen below, similar results were observed following the IHP stimulation of osteoblasts-like cells.

Figure 6:
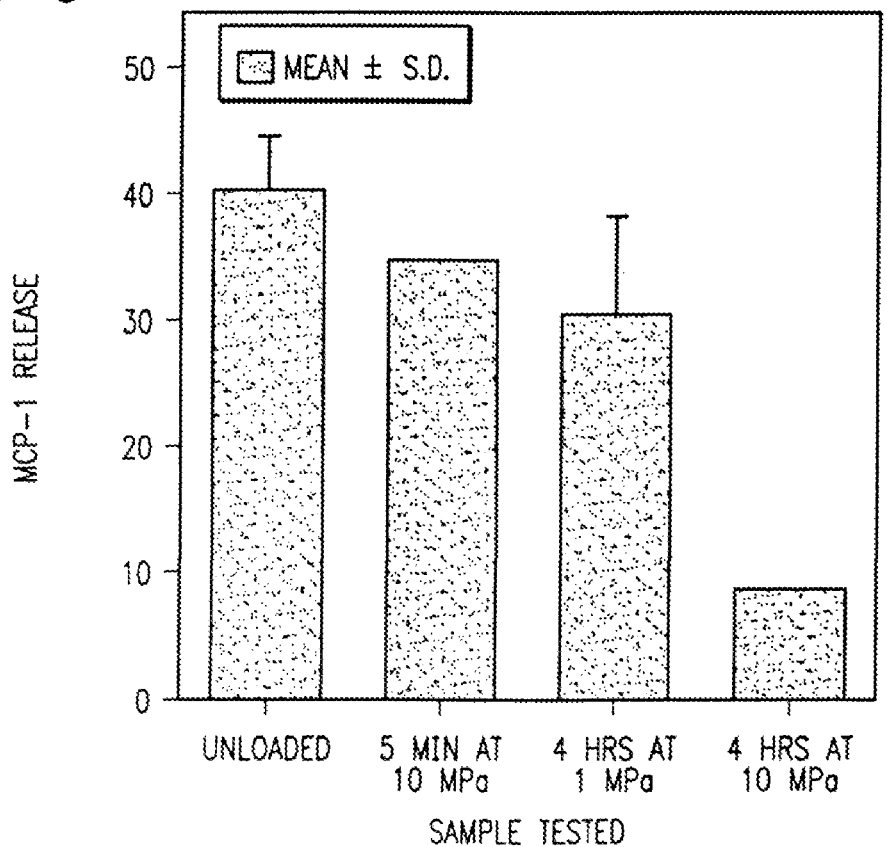
FIG. 6 is a graph showing the effects of interval loading with different magnitudes of intermittent hydrostatic pressure on release of macrophage chemoattractant protein-1 (MCP-1) from normal human articular chondrocytes.

FIG. 6 shows the effects of interval loading with different magnitudes of intermittent hydrostatic pressure on macrophage chemoattractant protein-1 (MCP-1) release from normal human articular chondrocytes.

MCP-1 represents one of a number of pro-inflammatory mediators that influence the immune state of tissues. A decrease in MCP-1 in chondrocytes is significant as a marker of a change in cell metabolism and in termination of inflammatory processes accompanying the cartilage degeneration or damage. The release of MCP-1 is normally associated with the recruitment of monocytes and macrophages, the cells of the immune system, that play a role in tissue destruction. Its decreased expression signals amelioration of cartilage damage.

As seen in FIG. 6, releases of MCP-1 from normal human articular chondrocytes is significantly decreased, approximately 8 times, following the application of IHP at 10 MPa for 4 hours.

Decrease observed in release of MCP-1 clearly shows that anti-inflammatory or anti-injury mechanism of the cartilage is less activated thus resulting in lesser degree of cartilage degeneration and destruction.

To determine whether the decrease in the release of MMP-1, MMP-2 or TGF-β following IHP is selective for those proteins involved in cartilage degeneration, studies were performed with fibroblast growth factor 1 which is not involved in such processes and thus should not react to the IHP. Results are seen in FIG. 7.

Figure 7:
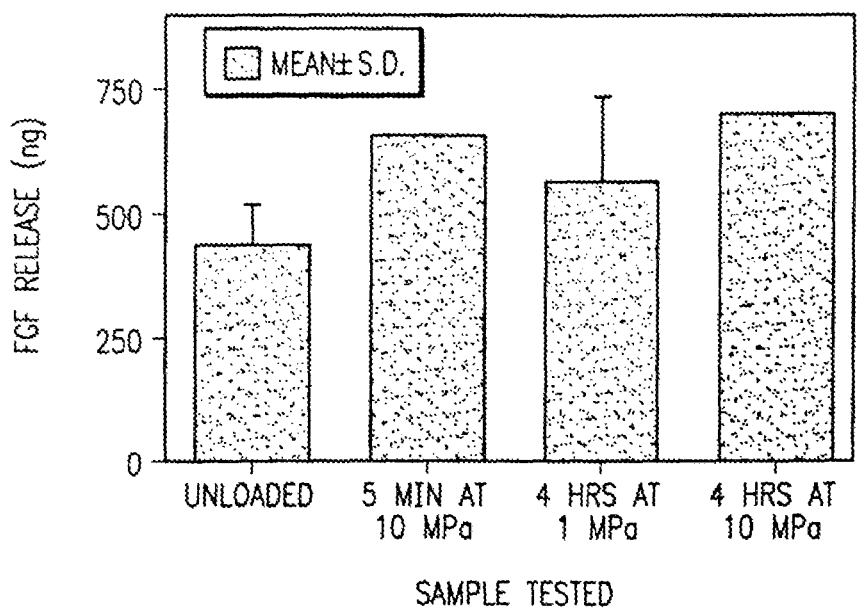
FIG. 7 is a graph showing the absence of an effect of interval loading with different magnitudes of intermittent hydrostatic pressure on fibroblast growth factor-1 (FGF-1) from normal human articular chondrocytes.

FIG. 7 shows the absence of an effect of interval loading with different magnitudes of intermittent hydrostatic pressure on fibroblast growth factor-1 (FGF-1) from normal human articular chondrocytes.

The FIG. 7 shows that not all growth factors respond to intermittent hydrostatic pressure but only those factors which are involved in cartilage degeneration or regeneration. The FIG. 7 also shows that the chondrocytes were not being damaged by the IHP and that the decreased release of MMP-2, TGF-β and MMP-1 was due to damaged cartilage.

The objective of the studies described in FIGS. 2-7 was to investigate whether the application of intermittent hydrostatic pressure on cartilage results in changes of matrix protein synthesis in isolated adult human articular chondrocytes.

FIGS. 2-7 cumulatively show that excessive or insufficient (5 minutes at 10 MPa or 4 hours at 1 MPa) loading of joint cartilage does not provide sufficient stimulus for cartilage repair and regeneration and in some cases, may even lead to increased degeneration and loss of function. Results seen in FIGS. 2-7 confirm that there is a correlation between IHP and between occurrence of beneficial changes in chondrocyte metabolic processes leading to cartilage regeneration.

Rehabilitation of joint function depends on repair and regeneration of diseased cartilage. A variety of experimental approaches described above confirm that mechanical loading influences synthesis of articular chondrocyte extracellular matrix components, i.e., aggrecan and type II collagen. However, until now no clear connection was shown to exists for mechanically-induced modulation of cartilage matrix gene expression establishing that mechanical IHP stimulation serves as impetus for repair and regeneration of cartilage. The above described results make the therapeutic intervention in vivo, in vitro and ex vivo feasible.

III. Time-Dependent Effects of IHP on mRNA Expression of Type II Collagen and Aggrecan Initial studies leading to this invention have shown that the hydrostatic pressure applied continuously does not lead to cartilage repair and regeneration measured by the increase or decrease metabolic activities of relevant protein synthesis. Such pressure applied for a short period of time resulted in increased expression of type II collagen mRNA while the continuously applied load did not maintain such increased expression. On the other hand, the aggrecan signal expression continued to increase throughout the duration of the load.

Studies documented in Section II have shown that there is a correlation between IHP and chondrocyte metabolic processes. The studies described in this section investigated time-dependent effects of IHP on type-II collagen and aggrecan mRNA expression in normal adult bovine articular chondrocytes in vitro.

The purpose of this study was to test whether the intermittent pressure applied to chondrocytes enhances type II collagen and aggrecan mRNA levels without stimulating type I collagen mRNA. The experimental approach relied on use of RT-PCR for relative quantification of collagen and aggrecan mRNA levels with respect to beta-actin mRNA as an internal reference signal.

Specifically, this study examined the effects of two types of loading regimens of intermittent hydrostatic pressure on expression of type II collagen and aggrecan mRNA in normal adult articular chondrocytes. The chondrocytes were isolated according to Example 1. A system for quantitative loading of adult articular chondrocytes used a high-density monolayer culture ($1.75 \times 10^5$ cells/cm$^2$) or aggregated cell clusters.

The loading of the cells with intermittent hydrostatic pressure was carried out either in a continuous pattern over a period of 24 hours or as interval loading with the load being applied for four hours per day according to Example 3. The metabolic response of the articular chondrocytes was determined using semi-quantitative reverse transcription polymerase chain reaction (RT-PCR) assays for type II collagen, aggrecan and beta-actin mRNA signal. Results are seen in FIGS. 8-12.

Figure 8:
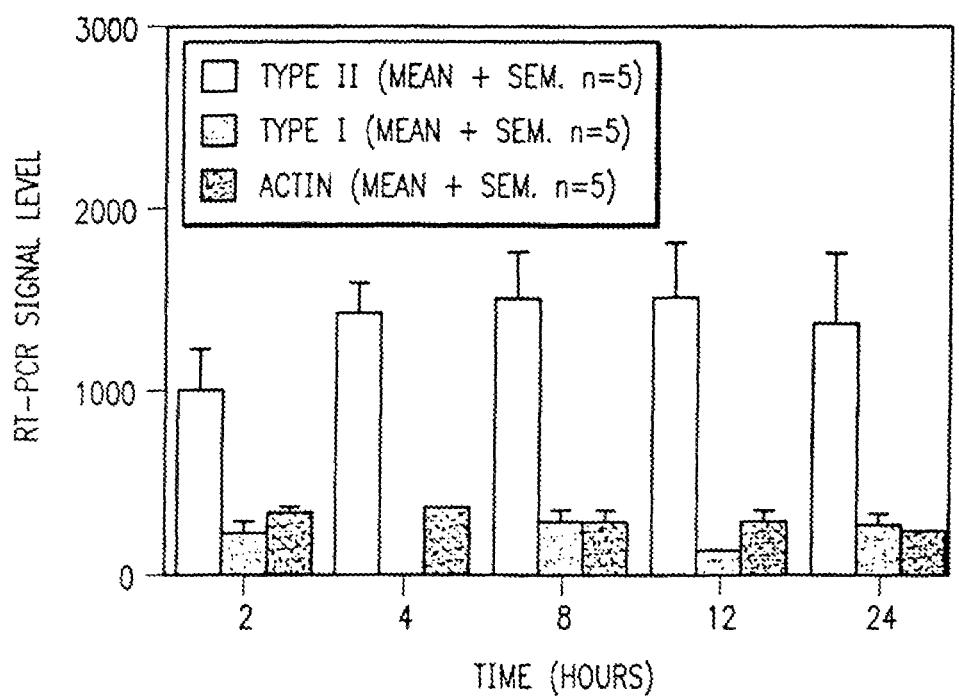
FIG. 8 is a graph showing RT-PCR signal levels for type II and type I collagen and beta-actin expression in unloaded control cells.

FIG. 8 is a graph showing RT-PCR signal levels for type II and type I collagen and beta-actin expression in unloaded high activity chondrocyte cultures maintained throughout designated testing periods 2-24 hours.

Figure 9:
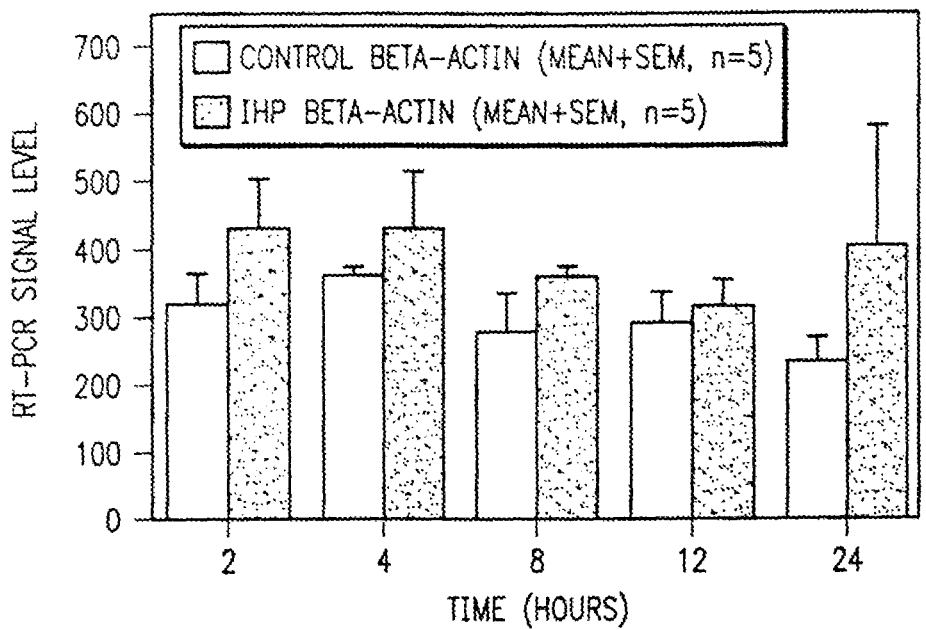
FIG. 9 shows signal levels for beta actin expression in cells exposed to IHP and in unloaded control cells.

FIG. 9 shows signal levels for β-actin expression in cells exposed to IHP and in unloaded control cells.

FIG. 8 shows signal levels determined by RT-PCR for type II collagen and β-actin expression in control cells obtained without stimulation at 2, 4, 8, 12 and 24 hours according to Example 3. RT-PCR conditions were as described in Example 4.

FIG. 8 shows RT-PCR signal levels for type II and type I collagen and β-actin expression in unloaded control cells is clearly detectable and does not change.

Articular chondrocytes plated and maintained as high-density monolayer cultures at atmospheric pressure (unloaded control cultures) did not exhibit significant variation with respect to signal levels for type II collagen mRNA or β-actin mRNA. These observations remained true over a time course of 2, 4, 8, 12 and 24 hours as seen in FIG. 8.

To determine a reference mRNA signal that would not change in response to applied IHP and thus would provide a reference point for comparison, β-actin was selected due to its relative abundance of mRNA and based on the location as an intracellular cytoskeletal protein.

FIG. 9 shows RT-PCR signal levels for β-actin expression in cells exposed to intermittent hydrostatic pressure and in unloaded control cells.

As seen in FIG. 9, exposure of chondrocytes to intermittent hydrostatic pressure did not alter β-actin mRNA signal levels over a time course of 2, 4, 8, 12 and 24 hours when compared to the unloaded control cells.

In contrast, application of IHP to normal chondrocyte in monolayer culture or aggregate culture demonstrated that type II collagen mRNA signal was not pronounced at loading periods of 4 and 8 hours and decreased thereafter. On the other hand, aggrecan mRNA, under the same conditions have shown different profile and continued to increase for 24 hours.

The results pertaining to type II collagen expression prompted examination of interval loading where IHP was applied for 4 hour periods followed by a period of recovery. The chondrocyte culture aggregates were exposed to intermittent hydrostatic pressure using continuous loading through a twenty-four hour period. Results are seen in FIGS. 10 and 11.

Figure 10:
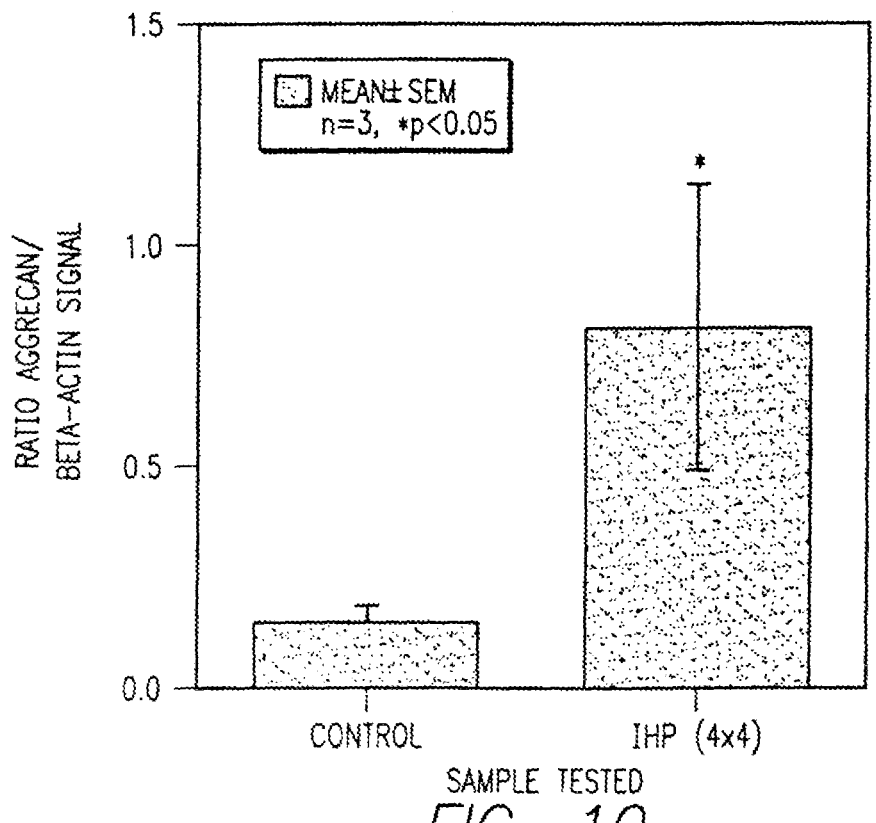
FIG. 10 shows RT PCR signal levels for aggrecan following exposure of high density monolayer cultures to IHP.

FIG. 10 shows RT-PCR signal levels for aggrecan following exposure of high-density monolayer cultures to intermittent hydrostatic pressure using interval loading at 4 hours per day followed by 20 hours recovery for 4 days.

Figure 11:
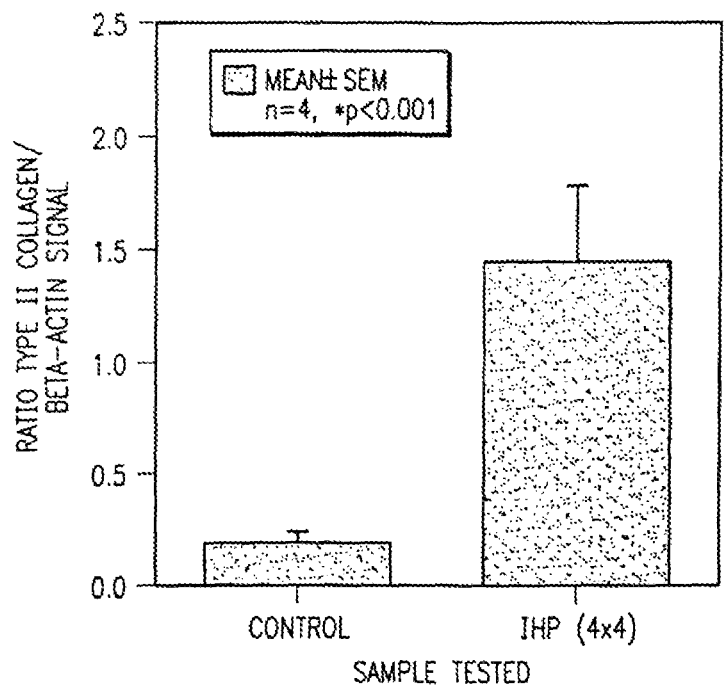
FIG. 11 shows RT PCR signal levels for type II collagen following exposure of high density monolayer cultures to IHP.

FIG. 11 shows RT-PCR signal levels for type II collagen following exposure of high-density monolayer cultures to intermittent hydrostatic pressure using interval loading at 4 hours per day followed by 20 hours recovery for 4 days. Under these loading conditions, signal level of the aggrecan mRNA increased approximately four times relative to the unloaded controls (FIG. 10). The change in loading protocol resulted in a about seven-fold increase in the type II collagen mRNA signal relative to unloaded controls (FIG. 11).

The results of the studies described above and illustrated in FIGS. 8-11 demonstrated that the chondrocytes responded to changed loading protocol to a pattern that included exposure to intermittent hydrostatic pressure for four hours followed by a twenty hour period of recovery, the RT-PCR signal attributable to type II mRNA was significantly elevated relative to signal representing β-actin mRNA. The aggrecan mRNA signal was also elevated.

These data show that mechanical IHP loading with an appropriate type of stimulus serves to modulate articular chondrocyte matrix macromolecule expression. The obtained results confirm that application of specific loading regimens facilitates the repair and regeneration of articular cartilage and contributes to the successful production of composite transplantable cartilage grafts.

The documented effects of hydrostatic pressure on the chondrocytes shows that the specific loading regiments provide an effective stimulus to modulated cartilage extracellular matrix macromolecules synthesis and to initiate reactions connected with repair and regeneration of damaged cartilage and type II collagen.

IV. Effects of Intermittent Hydrostatic Pressure on TGF-β1 and MMP-2 Expression in Osteoblast-Like Cells Mechanical stress generated during normal weight bearing activities contributes to bone structure and function through a specific cycle involving osteoblastic formation and osteoclastic resorption. Maintenance of normal bone homeostasis in response to loading history involves a number of hormones, cytokines and growth factors.

Following the above described findings, this study investigated whether intermittent hydrostatic pressure (IHP) modulates expression of the pleiotrophic growth factor, namely, transforming growth factor-beta 1 (TGF-β1), in bone cells MG-63, HOS TE85, and whether it functions as a mechanical signal for modulation of bone cell metabolism. To this end, the effect of IHP on osteoblast expression of TGF-β1, which is known to influence osteoblast proliferation and phenotypic expression of bone specific proteins was tested. Additionally, expression of matrix metalloproteinase MMP-2 was investigated.

Figure 12:
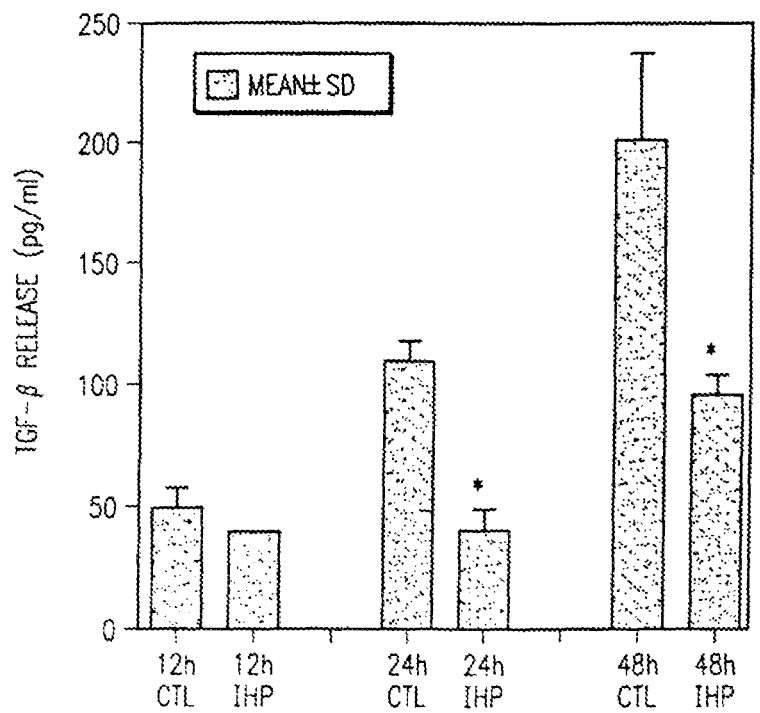
FIG. 12 shows time course analysis for TGF-β1 release from MG-63 cells exposed to intermittent hydrostatic pressure (10 MPa).
Figure 13:
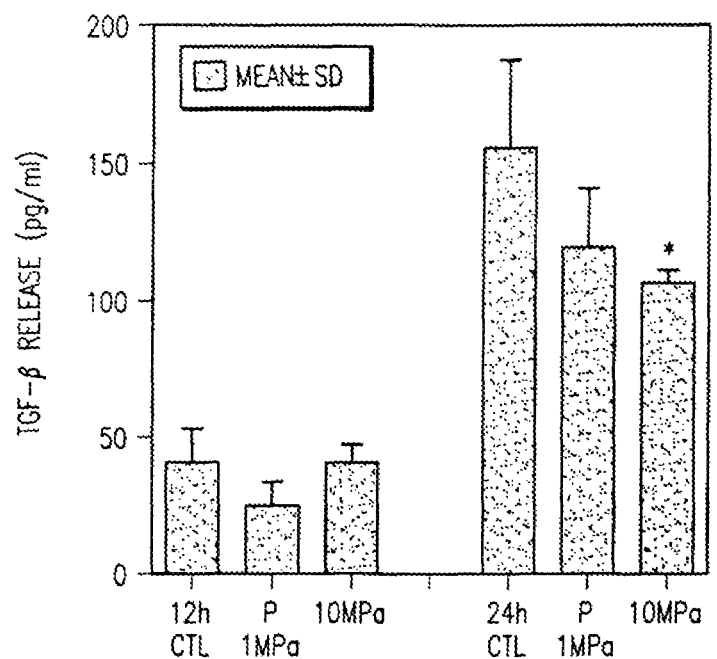
FIG. 13 depicts dose response effects of intermittent hydrostatic pressure on the TGF-β1 release from MG-63 cells.
Figure 14:
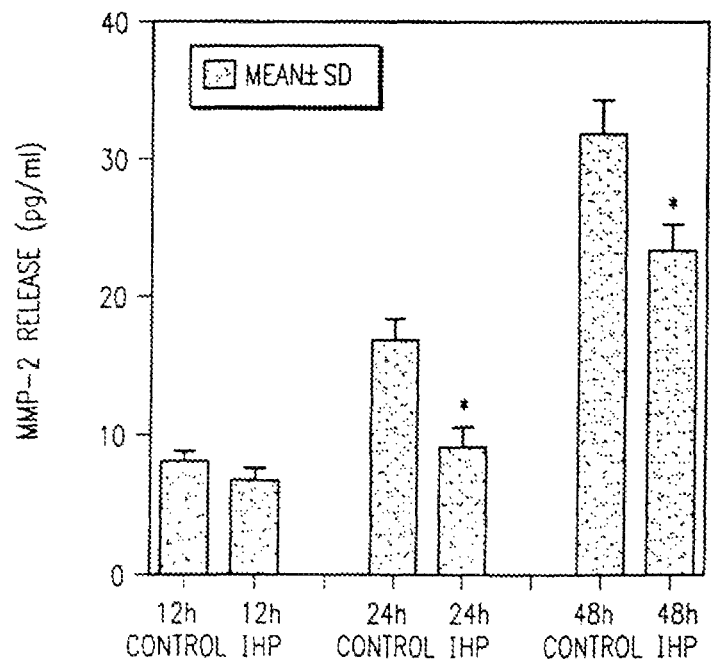
FIG. 14 shows time course analysis for MMP-2 release from MG-63 cells exposed to IHP.

Results are seen in FIGS. 12-14. FIGS. 12-14 illustrate the effect of IHP on TGF-β protein production or MMP-2 expression in osteoblast-like cells MG-63.

FIG. 12 shows time course analysis for TGF-β1 release from MG-63 cells exposed to IHP at 10 MPa. FIG. 13 shows dose response effects of IHP on the TGF-B1 release from MG-63 cells. The bar and the vertical line in FIGS. 12 and 13 represent the means±SD, respectively (n=3), $p<0.05$ compared with control.

The concentration of TGF-β1 protein in the conditioned medium of MG-63 was investigated by ELISA. With MG-63 cells, no significant change in TGF-β1 release was observed following a 12 hour exposure to IHP as shown in FIG. 12. However, as also seen in FIG. 12, application of IHP for 24 and 48 hours decreased release of TGF-β1 from the MG-63 cells by 65% ($p<0.05$) and 53% ($p<0.05$), respectively, relative to the unloaded cells. Similar results were observed for HOS TE85 cells (data not shown).

A second series of studies seen in FIG. 13 examined the dose response effect of IHP on TGF-β1 expression with MG-63 cells. A 12 hour exposure to IHP at a level of 1 and 10 MPA did not alter TGF-β1 release. After 24 hours application of IHP at either 1 MPA or 10 MPA, as seen in FIG. 13, TGF-β1 release into the medium was inhibited by 23% and 31% respectively, when compared to unloaded cells.

FIG. 14 depicts a time course analysis for MMP-2, release (pg/ml) from MG-63 cells exposed to IHP as quantified by ELISA.

FIG. 14 shows quantification of the release of MMP-2 in the conditioned medium using ELISA. A similar pattern was observed in the zymographic analysis (data not shown). As seen in FIG. 14, following 24 and 48 hours of exposure to IHP, MMP-2 release was significantly inhibited by 46% and 28%, respectively, relative to controls. Application of IHP under the same conditions also decreased release of TIMP-1 in the conditioned medium of the osteoblast-like cells.

Following 24 and 48 hours of exposure to IHP, TIMP-1 release was significantly inhibited by 63% and 29%, respectively, relative to the unloaded cells. MMP-1 and MMP-9 were not detected in medium samples from cells exposed to IHP or unloaded cells at any time period (data not shown).

Zymographic analysis illustrated showed that MMP-2 was the prominent matrix metalloproteinase released by the MG-63. In the presence of IHP zymography demonstrated an inhibition in the release of the latent 72 kD form of MMP-2 and both of the activated forms, 68 kD and 62 kD, in medium samples from cells exposed to IHP for 24 and 48 hours when compared to samples from unloaded cells.

VI. Therapeutic Utility

The therapeutic method of the invention is useful in the fields of orthopedic surgery, rheumatology, sport and rehabilitation medicine. The method of the invention permits formation of de novo and regeneration of diseased or injured cartilage, particularly articular cartilage. The methods permit external treatment of cartilage in situ by applying externally a device administering hydrostatic pressure to a diseased or injured joint intermittently for several hours followed by the periods of recovery. The method also permits ex vivo regeneration of cartilage or usable cartilage grafts removed from the diseased or injured joint, regenerating such cartilage or graft to a degree where both the mechanical and biochemical properties of the cartilage are restored to normal levels and replacing the graft into the joint once cartilage collagen matrix is restored. Additionally, the method permits the in vitro treatment of cartilage and bone cells and cell cultures into functional tissue suitable for transplantation and de novo formation and production of healthy normally functioning cartilage and other mesenchymally-derived cells.

Example 1: Chondrocyte Isolation

This example describes procedure used for isolation of chondrocytes.

Adult bovine articular chondrocytes were isolated from full thickness cartilage dissected from radiocarpal joints obtained fresh from a local abattoir.

The cartilage cells were released from the matrix by incubation in 15 ml of Dulbecco's modified Eagle's medium (DMEM) containing gentamicin (50 ug/ml) and a mixture of bacterial collagenases, type II and type IV, (Worthington, Freehold, N.J.) at a final concentration of 0.6 mg/ml each in 15 ml of Dulbecco's Modified Eagle's Medium/Ham's F12 (DMEM/F12, Gibco BRL, Grand Island, N.Y.) containing 25 µg/ml gentoamicin (Sigma, St. Louis, Mo.). The cartilage samples were incubated for a total of 18 hours at 37° C. in 7.5% $CO_2$ and 100% humidity to ensure complete digestion. Chondrocytes released from matrix were filtered through a nylon mesh filter to isolate single cells. The cells were subsequently collected by repeated centrifugation at 600×g with the cells being resuspended and collected in Dulbecco's phosphate buffered saline (3×50 ml).

A final cell pellet was suspended in the serum-free DMEM/F12 medium and the cells counted in a hemacytometer with viability assessed by Trypan Blue exclusion. Normal viability obtained for chondrocytes under these conditions was greater than 95%.

Chondrocytes were then plated on 60 mM tissue plates and the culture were maintained at 37° C. in a humidified atmosphere of 7.5% $CO_2$ in air. For attachment in serum free conditions, the individual plates were pre-treated overnight with poly-D-lysine (Sigma, 0.1 mg/ml) and washed twice with PBS without calcium or magnesium. Cells were plated at a density of $1\times10^5$ cells/cm$^2$.

Example 2: Serum Containing or Serum-Free Medium

This example describes a composition of serum containing or serum-free medium.

Serum containing Dulbecco's modified Eagle's medium (DMEM) contained dialyzed heat-inactivated fetal bovine serum at a concentration of 10% v/v. Serum-free medium consisted of a 1:1 mixture of Ham's F12/DMEM supplemented with selenium, and liposomes. Liposomes were prepared by dissolving lecithin, cholesterol, sphingomyelin, and vitamin E acetate in 1 ml of 2:1 chloroform/methanol (vol/vol) which is dried under $N_2$. One ml of DMEM/F12 was added and the lipid mixture was then sonicated 3× for intervals of 3 minutes each, using a microtip with a 70% duty cycle. This liposome stock was made up at 1,000× the final concentration, kept under $N_2$, and stored at 4° C. In some experiments, ascorbate was added to the medium at a concentration of 50 µg/ml.

Example 3: Mechanical Loading with Intermittent Hydrostatic Pressures

This example describes loading protocol and conditions for applying intermittent hydrostatic pressure.

Hydrostatic pressure was cyclically applied at a loading dose of 10 MPA and at a frequency of 1 Hz. The intermittent hydrostatic pressure was applied continuously with cells removed at periods of 2, 4, 8, 12 and 24 hours, or through an interval loading protocol with the cells removed after a 4 day period during which intermittent hydrostatic pressure was applied for and limited to 4 hours per day followed by 20 hours of recover. This was repeated daily for four days or more. Each experimental time point was tested in triplicate and each experiment was carried out for a minimum of three independent trials.

The pressure was generated with a commercially available stainless steel pressure vessel interfaced to a servo-hydraulic loading instrument seen in FIG. 1. The design provided for the complete evacuation of air from the system so the application of pressure was purely hydrostatic. The culture plates were loaded within sterile heat-sealed bags containing forty-five ml of culture medium (DMEM/F12 1:1 with 30 mM HEPES adjusted to pH 7.4 for pH stability in the absence of carbon dioxide).

Temperature control was achieved by partial immersion of hydrostatic loading vessel within a circulating water bath and maintained at 37° C. No measurable change in temperature occurred over loading periods up to 96 hours. Control cultures were maintained under identical conditions in heat sealed bags and placed in an identical container placed in the same temperature controlled water bath as the loaded cultures.

Example 4: Analysis of Aggrecan and Type II Collagen mRNA Signal Levels (RT-PCR)

This example describes the procedure used for analysis of mRNA signal levels of aggrecan and type II collagen by RT-PCR.

To permit multiple samples to be tested for each loading condition, an experimental approach using semi-quantitative RT-PCR was used for analysis of aggrecan and type II collagen mRNA signal levels as described in *J. Orthop. Res.*, 15:94 (1997) for MMP-9 expression. Immediately at the cessation of loading, total RNA from the cells exposed to intermittent hydrostatic pressure and from the unloaded cells was extracted from the cells by the quanidinium isothiocynate method described in *Biochemistry*, 18:5296 (1979) with a commercially available tri-reagent (Sigma, St. Louis, Mo.). A typical yield of cellular RNA per 60-mm plate was 5 micrograms.

All RNA preparations were routinely screened on agarose gels for integrity of ribosomal RNA. Total RNA concentrations was determined by spectrophotometry and adjusted to 200 ng/ul for reverse transcription using random hexamer priming. The mRNA sample was converted to single stranded cDNA using m-MLV reverse transcriptase (Gibco-BRL) in the presence of RNase inhibitor (5-Prime, 3-Prime, Inc., Boulder, Co.) and in the presence of 500 uM dNTPs (Perkin Elmer Cetus, Norwalk, Conn.). The reaction was carried out at 37° C. for 15 minutes, 42° C. for 10 minutes, 47° C. for 10 minutes and finally raised to 99° C. to inactivate the reverse transcriptase. The reaction mixture was diluted 10× and used for PCR.

The target sequences in the reverse-transcripted cDNA samples were amplified by PCR, using sequence-specific oligonucleotide primers designed to yield approximately 200-bp sequences that span different exons within the aggrecan (*Anal. Biochem.*, 225:356 (1995)) and type II collagen (*Arch. Biochem. Biophys.*, 314:90 (1994)) genes. The primer sets for aggrecan and type II collagen were based on published sequence data for these genes.

DNA size analysis and DNA sequencing of the specific products determined the validity of the products generated using the primer sets.

PCR was carried out with 1.0 ul of cDNA in a 0.5 ml reaction tube containing 1.5 ul of PCR master mix; the reaction was initiated at 65° C. to avoid nonspecific annealing. The PCR master mix contained 125 mM Tris HCl, 50 mM ammonium sulfate, 3.75 mM magnesium chloride, 62.5 mM dNTPs, 300 nM of each downstream and upstream primers, and 0.625 U/ml Tfl DNA polymerase (Epicentre Technologies, Madison, Wis.). $^{32}P$-α-dCTP at 3,000 Ci/mmol (Amersham NEN-Corp.) was added to the master mix to make 0.1 mCi/ml final concentration for random radiolabelling of amplified products. The total reaction volume at the start of PCR was 2.5 ml.

For comparison of relative expression, 0.5 ml of a primer solution containing 900 nM of an oligonucleotide primer set for amplification of the 3' untranslated region of β-actin, 50 mM Tris HCL, 20 mM ammonium sulfate, 1.5 mM magnesium chloride was added at the tenth cycle and amplified in the same reaction tube. β-actin mRNA signal served as an internal control to monitor for tube-to-tube variations in amplification conditions and differences in the initial concentration or loading of cDNA. The thermocycle program included one cycle of 95° C. for 3 minutes for initial heating, followed by repeated cycles of 95° C. for 1 minute and 65° C. for 1 minute. Final extension was carried out at 72° C. for 5 minutes. The total cycle number employed in this study was 30 cycles for aggrecan and type II collagen and 26 cycles for β-actin.

The amplified products from PCR were separated on 5% polyacrylamide gels and the gels were directly analyzed using the Phospholmager (Molecular Dynamics, Sunnyvale, Calif.) Relative expression of the mRNA was expressed as specific signal levels and as a ratio of signal of the aggrecan and type II to the β-actin signal.

Example 5: Statistical Methods

This example describes the details of statistical methods used for evaluation of results obtained in Examples 3 and 4.

Significance of differences between loaded and unloaded samples were examined using the general linear method for one-way analysis of variance (NOVA) with the addition of Tukey's correction for multiple comparison testing (SAS, Gary, N.C.).

Determination of the mRNA signal levels by semi-quantitative RT-PCR techniques provided sufficient differences between treated and untreated samples so that a power level was achieved to determine significance at $p<0.05$ with five independent trials. In the case of the mRNA quantification, the hypothesis being tested was that a change in matrix gene expression occurred relative to expression of β-actin. The β-actin expression was determined not to change in response to intermittent hydrostatic pressure. This permitted paired t-test to be used to test for significance from the different culture samples.

Example 6: Human Osteoblast Cell Culture

This example describes procedure used to prepare human osteoblast cell culture.

Human osteoblast-like cells, MG-63 and HOS TE85, were purchased from the American Type Culture Collection (Manassas, Va.).

The cells were cultured in 60 mM dishes with alpha minimal essential medium (alpha-MEM) (Gibco, Grand Island N.Y.) containing 10% fetal bovine serum (Gibco) and antibiotic-antimycotic (Gibco; 100 U/ml penicillin, 100 µg/ml streptomycin, 0.25 µg/ml amphotericin B), at 37° C. in an atmosphere of air containing 5% $CO_2$.

Confluent cultures were incubated for an additional 24 hours in the absence of serum to establish growth arrest. Culture medium was removed and each culture plate was placed into a heat sealed bag containing 40 ml of serum-free alpha-MEM supplemented with 0.1% BSA, 15 mM HEPES, ascorbic acid (50 µg/ml) and Na-β-glycerolphosphate (10 mM). The heat sealed bags were immersed in a high pressure vessel filled with water and IHP (1 or 10 MPA at a frequency of 1 Hz) was applied for 12, 24 and 48 hours.

Control cultures were maintained at atmospheric pressure. Both the pressure vessel and unloaded control cultures were maintained at atmospheric pressure. Both the pressure vessel and unloaded control cultures were maintained in the water bath during testing period to maintain the temperature at 37° C. Culture medium samples were collected and stored at −20° C. until use.

To study the mRNA stability, actinomycin D (2.5 mg/ml) was dissolved in methanol and applied to cultures at a final concentration of 5 µM.

Human chondrocytes were obtained in the same way but were pretreated with trypsin 0.1 mg/ml to remove protease and collagen inhibitors.

Example 7: Measurement of TGF-β Protein Level in the Conditioned Medium

This example describes a method used for measurement of TGF-β protein level in the medium.

Matched pair antibodies against TGF-β1 were purchased from R & D Systems (Minneapolis, Minn.). Latent TGF-β1 in the conditioned medium was activated by 1N HCl and conditioned medium samples were neutralized by the addition of 1.2 M NaOH/0.5 M HEPES buffer. Total TGF-β1 was measured using enzyme-linked immunosorbent assays (ELISAs). All samples were analyzed in triplicate. The optical densities were determined on an ELISA reader at 450 nM with background correction at 595 nM.

Example 8: Northern Blot Analysis for TGF-β

This example describes conditions used for TGF-β Northern blot analysis.

Total RNA was extracted from the cells by the method described in *Anal. Biochem.*, 162:156 (1987).

For a Northern blot analysis, 10 μg of total RNA was denatured and fractioned on a 1% agarose 1.1 M formaldehyde gel and stained with ethidium bromide to determine the integrity of the 28S and 18S bands. Transfer to a nylon membrane was performed by standard methods. The membranes were hybridized to $^{32}$P-labeled cDNA probes for TGF-β1 (ATCC) and GAPDH (ATCC).

The radioactivity of the each hybridized probe was analyzed using a PhosphorImager (Molecular Dynamics, Sunnyvale, Calif.).

Example 9: Method for Statistical Analysis

This example describes the method for statistical analysis of studies described in Examples 7 and 8.

The significance between treated and control groups was determined using ANOVA and unpaired Student's two-sample t-test (two-tailed) using Bonferroni approximation for multiple comparisons. All values are given as the means±SD. Northern blotting results were expressed as a ratio of the target mRNA signal (TGF-β1) over the housekeeping mRNA signal (GAPDH). Differences in mRNA ratios observed with and without IHP treatment were assessed using the Mann-Whitney U-test with a p<0.05 representing significance.

Example 10: Zymography

This example describes conditions used for zymography.

Medium samples were activated by incubating in 1.0 mM 4-aminophenylmercuric acetate (APMA) for one hour at 37° C. The samples were subsequently mixed with sample buffer and run in 10% SDS-polyacrylamide gels impregnated with 1 mg/ml gelatin. The gels were washed with water and soaked for one hour in 2.5% Triton X-100 in water. After a sixteen hour exposure at 37° C. in substrate buffer (0.05 M Tris-HCl, pH 8.0, 5 mM $CaCl_2$, and 0.02 $NaN_3$) the gels were stained in a solution of 0.5% Commassie Blue R-250 in 30% ethanol and 10% acetic acid, then destained in water to visualize gelatinolytic activity.

Example 11: Measurement of Peptide of MMPs and TIMP-1 in the Conditioned Medium

This example describes a method used for determination of presence of MMP-1, MMP-2, MMP-9 and TIMP-1 proteins in medium.

At the completion of loading, the medium samples were collected from each bag and the concentration of MMP-1, MMP-2, MMP-9 and TIMP-1 proteins were measured using enzyme-linked immunosorbent assay (ELISA) kits (Oncogene, Cambridge, Mass.) according to the manufacturer's instructions.

Example 12: Northern Blot Analysis for MMP-2 and TIMP-1

This example describes the conditions for Northern blot analysis for MMP-2 and TIMP-1.

Total RNA was extracted from the cells by the same method as described in Example 8. For a Northern blot analysis, 10 μg of total RNA was denatured and fractionated on a 1% agarose 1.1 M formaldehyde gel and stained with ethidium bromide to determine the integrity of the 28S and 18S bands. Transfer to a nylon membrane was performed by standard methods.

The membranes were hybridized to $^{32}$P-labeled cDNA probes for MMP-2 and TIMP-1 (ATCC, Manassas, Va.). The radioactivity of the each hybridized probe was analyzed using a Phosphor Imager (Molecular Dynamics, Sunnyvale, Calif.).

Example 13: Determination of mRNA Stability

This example describes a method used for determination of mRNA stability.

The stability of the mRNA following a mechanical loading test period of 24 hours was determined by the addition of actinomycin D to the cells according to Example 6.

Actinomycin D was added at a concentration of 2 micrograms per milliliter in four milliliters of serum free culture medium. The cells were maintained for test periods of 0, 1, 2 and 4 hours prior to isolation of total cellular RNA. The analysis of mRNA signal levels was as described in Example 11 for Northern blotting. Stability of mRNA in control cultures was determined as described with cells not exposed to IHP.

Example 14: Statistical Analysis

This example describes a method for statistical analysis of results obtained in studies described in Examples 10-12.

The significance between treated and control groups was determined using ANOVA and unpaired Student's two-sample t-test (two-tailed) using Bonferroni approximation for multiple comparisons. All values are given as the means±SD.

What is claimed is:

1. A hydrostatic pressure vessel comprising human chondrocytes isolated from a human having osteoarthritis, wherein the chondrocytes are present within a scaffold.

2. The hydrostatic pressure vessel of claim 1, wherein said chondrocytes are human osteoarthritic chondrocytes.

3. The hydrostatic pressure vessel of claim 1, wherein said chondrocytes are in a graft configured for autologous transplantation.

4. The hydrostatic pressure vessel of claim 1, wherein said chondrocytes are in a cell culture medium.

5. The hydrostatic pressure vessel of claim 1, wherein the chondrocytes comprise aggrecan levels of from 0.1% to 1%, wet weight.

6. The hydrostatic pressure vessel of claim 1, wherein the chondrocytes comprise type II collagen levels of from 1% to 10%, wet weight.

7. The hydrostatic pressure vessel of claim 1, wherein the chondrocytes comprise higher levels of at least one of MMP-2, IL-6, and MCP-1, as compared to physiological levels of non-osteoarthritic chondrocytes.

8. The hydrostatic pressure vessel of claim 1, wherein the chondrocytes comprise aggrecan levels of from 4% to 7%, wet weight.

9. The hydrostatic pressure vessel of claim 1, wherein the chondrocytes comprise type II collagen levels of from 10% to 20%, wet weight.

10. The hydrostatic pressure vessel of claim 1, wherein the chondrocytes comprise lower levels of at least one of MMP-2, IL-6, and MCP-1, as compared to chondrocytes of degenerated cartilage.

\* \* \* \* \*

UNITED STATES PATENT AND TRADEMARK OFFICE
CERTIFICATE OF CORRECTION

PATENT NO. : 10,655,104 B2
APPLICATION NO. : 14/553869
DATED : May 19, 2020
INVENTOR(S) : R. Lane Smith et al.

It is certified that error appears in the above-identified patent and that said Letters Patent is hereby corrected as shown below:

On the Title Page

Item (57) Replace the abstract with the following:
A method for *in vivo, ex vivo* and *in vitro* regeneration of cartilage and collagen. *In vivo, ex vivo* and *in vitro* regeneration and *de novo* formation of articular cartilage and collagen by intermittently applied hydrostatic pressure. The application of external interval loading consisting of repeated periods of applied hydrostatic pressure followed and interrupted by periods of recovery. The application of the intermittent hydrostatic pressure at physiological levels 5-10 MPA for an interval of 4 hours followed by a recovery period up to about 20 hours, said pressure applied to the cartilage cells *in vitro*, explants of cartilage *ex vivo* and *in vivo* to cartilage that remains intact within the joint space of diarthrotic joints. The interval loading results in the selective inhibition of matrix degrading enzymes, pro-inflammatory cytokines and chemokines that attract inflammatory cells into the joint cavity and in selective decrease of gene expression of growth factors that are inhibitory to type II collagen expression.

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*